United States Patent [19]

Quaid et al.

[11] Patent Number: 5,123,903
[45] Date of Patent: Jun. 23, 1992

[54] DISPOSABLE ASPIRATION SLEEVE FOR ULTRASONIC LIPECTOMY

[75] Inventors: Joel K. Quaid; Peter LeVay, both of Santa Barbara, Calif.

[73] Assignee: Medical Products Development, Inc., Santa Barbara, Calif.

[21] Appl. No.: 652,452

[22] Filed: Feb. 7, 1991

Related U.S. Application Data

[63] Continuation of Ser. No. 392,730, Aug. 10, 1989, abandoned.

[51] Int. Cl.⁵ .............................................. A61B 17/20
[52] U.S. Cl. .................................... 604/22; 604/902; 606/169; 128/24 AA
[58] Field of Search ............... 604/22, 902; 128/24 A; 606/128, 168-169, 171

[56] References Cited

U.S. PATENT DOCUMENTS

| | | | |
|---|---|---|---|
| 3,589,363 | 6/1971 | Banko et al. | 604/22 |
| 3,805,787 | 4/1974 | Banko | 604/22 |
| 3,956,826 | 5/1976 | Perdreaux, Jr. | 128/24 AA |
| 3,990,452 | 11/1976 | Murry et al. | 606/169 |
| 4,425,115 | 1/1984 | Wuchinich | 604/22 |
| 4,526,571 | 7/1985 | Wuchinich | 604/22 |
| 4,634,419 | 1/1987 | Kreizman et al. | 604/22 |
| 4,792,327 | 12/1988 | Swartz . | |
| 4,808,154 | 2/1989 | Freeman . | |
| 4,815,462 | 3/1989 | Clark . | |

Primary Examiner—C. Fred Rosenbaum
Assistant Examiner—C. Maglione
Attorney, Agent, or Firm—Michael G. Petit

[57] ABSTRACT

A disposable aspiration sleeve for use with an ultrasonic handpiece, which ultrasonic handpiece includes an ultrasonic horn wherein the cylindrical aspiration sleeve, which is provided with a vacuum tube coupling nipple, is removably mounted at its base to the handpiece and is provided with a supporting mount or mounts on its interior surface positioned in such a manner that the supportive mount or mounts each touches the horn at a vibratory node, thereby acoustically isolating the interior wall portion of the cylindrical sleeve from the ultrasonic horn or tip member. The addition of an aspiration sleeve with supporting mount or mounts positioned to rest upon the ultrasonic horn at one or more vibrational nodes enables the use of inexpensive plastic for construction, provides the necessary acoustical isolation for maximization of energy transfer to the tip of the ultrasonic horn, prevents transmission of ultrasonic energy from the horn to surrounding tissue, and creates an annular conduit between the sleeve and the horn for tissue aspiration which cannot be occluded by the sleeve touching the ultrasonic horn.

2 Claims, 1 Drawing Sheet

DISPOSABLE ASPIRATION SLEEVE FOR ULTRASONIC LIPECTOMY

CROSS-REFERENCE TO RELATED APPLICATIONS

This is a continuation of application Ser. No. 07/392,730, filed Aug. 10, 1989, now abandoned.

BACKGROUND OF THE INVENTION

1. Field of the Invention

The present invention generally relates to a medical instrument useful for performing ultrasonic tissue disruption and removal, and more specifically relates to an aspiration sleeve member for use with an ultrasonic lipectomy device.

2. Background

Suction-assisted lipectomy is a procedure for removing fatty tissues of the body through aspiration. In suction lipectomy, an incision is made through which a thin tubular metal aspirating cannula is pushed to scrape and vacuum away tissue. In order to facilitate uniform fat removal in the targeted region, the surgeon typically massages the flesh in the area of the aperture in the tip of the lipectomy cannula while, at the same time, thrusting the rod back and forth within the tunnel. This is an extremely traumatic method for the patient as it involves blind blunt dissection, cutting and tearing of tissue. As all tissue in the area is traumatized, the patient is visibly bruised for several weeks. This technique is physically exhausting for the surgeon and control is difficult because of the force and repeated rapid thrusts required to scrape, break down and extract the tissue.

The trauma to the tissue associated with this method of high suction and physical tearing of the fatty tissue from the body is undesirable. Suction lipectomy does not permit selective extraction of adipose (fat) tissue. Any tissue in the target area, including blood vessels, subcutaneous muscle, etc., is destroyed or traumatized. Deaths have been reported as a result of fluid loss and blood clots. Suction lipectomy is also slow, increasing the risk to the patient of complications of general anesthesia.

It would be desirable and advantageous to devise an improved cannula which would assist the surgeon in the lipectomy procedure by 1) enabling selective removal of fatty tissue while reducing trauma to other tissues in the area, 2) decreasing the effort required to break down the tissue, thereby decreasing surgeon fatigue and permitting more delicate maneuvering of the cannula, and 3) decreasing the amount of time necessary to complete the procedure.

Recently, ultrasound has been used to assist in the removal of fatty tissue. A typical ultrasonic aspiration unit consists of four basic components: a power supply, a source of vacuum, a piezoelectric or electrostrictive converter, and an ultrasonic horn on a handpiece. The power supply converts 115 volt 60-cycle energy into higher frequency electrical energy. The converter transforms the higher frequency electrical energy from the power supply into mechanical vibrations. The heart of the converter is most commonly a lead zirconate titanate electrostrictive element (crystal) which expands and contracts at its resonant frequency when excited by electrical energy. The electrostrictive element is highly efficient and energy conversion from electrical to mechanical energy is better than 90%. The ultrasonic horn transfers mechanical vibratory energy from the converter to the working tip of the horn.

Ultrasonic horns are made of materials which have a good combination of acoustical and mechanical properties. An exponential horn has a cross-sectional area which follows an exponential equation. The gradual taper of exponential horns distributes internal stresses over a greater length so that lower peak stress results. Consequently, these horns have desirable stress curves but low gain factors and are used mainly for applications requiring high force and low amplitude such as insertion into fatty tissue. An exponential horn has been found to be adequate for ultrasonic-assisted liposuction.

In biological applications of acoustic energy the important factor is the localization of energy experienced at a particular point in the acoustical propagation path such as at the tip face of the horn and minimization or prevention of energy dissipation along the horns length. Almost all biological effects depends upon the acoustic energy intensity per unit area. The acoustic wave emanating from the horn tip face will produce rapid cell disruption due to acoustic absorption. Localization of the energy used to obtain cellular disruption at a point remote from the transducer without undue physical effect on the intervening medium is paramount. A concern in liposuction applications is inappropriate transfer of energy and heating that can damage tissue in areas away from the target area.

In ultrasonic-assisted liposuction devices, much energy is lost by friction when energy is transferred from the length of the ultransonic horn to the surrounding tissue. This creates heat which can damage the tissue.

Although in suction lipectomy aspirator tubing is mounted directly on the handpiece, this results in inefficient operation of the horn in ultrasonic devices. The vibration of the handpiece and movement through the tissue causes the sleeve to come in contact with the ultrasonic probe, resulting in energy dissipation away from the tip and heating of sleeve and tissue.

In all lipectomy devices the inner surfaces of the aspirator channel formed by the sleeve are very difficult to clean. A disposable sleeve is desirable but has not been possible due to the rigidity and strength required in a sleeve mounted at a single point. With this in mind, it would be desirable to have mountings for the sleeves of ultrasonic lipectomy handpieces which would enable the use of less expensive and therefore disposable materials. However, these mountings cannot interfere with the energy transfer to the tip of the ultrasonic horn.

3. Description of Prior Art

U.S. Pat. No. 4,792,327 to Swartz describes an improved suction lipectomy or cannula having an inner and outer tube, the outer tube containing an aspiration aperture. A mechanism inside the handle of the device causes the inner tube to rotate creating a traveling hole effect along the aspiration aperture. This is to obviate the necessity of the surgeon repeatedly pushing the cannula in and out. A valve system is also disclosed to allow the surgeon to maintain negative pressure in the vacuum line leading to the cannula while still allowing the cannula itself to be vented to ambient pressures.

Clark, in U.S. Pat. No. 4,815,462, describes a suction lipectomy device which includes a generally hollow tubular housing with a cutting blade and a drive shaft wholly positioned within the conduit of the tube. The cutting blade is releasably connected to an electric motor in the housing for rotating the blade and a suctionline also runs into the front end of the housing to remove severed tissue sucked through the blade and/or conduit.

Unlike the present invention, both of these devices are designed to be used with suction-lipectomy instruments not assisted by ultrasound. They coud not be used with ultrasound-assisted suction lipectomy.

Ultrasonic aspiration devices have long been used in the area of opthalmology for removal of cataract lens from the human eye. A technique known as phacoemulsification is used wherein an ultrasonic vibrating tip is inserted through a small corneal incision of several millimeters. The ultrasonic tip operably emulsifies the cataract in situ. An outer coaxial sleeve extends along the length of the ultrasonic tip and permits a simultaneous injection of a saline flushing solution to suspend particles of lens material and to simultaneously cool the vibrating tip member. The ultrasonic tip is fashioned with an axial bore and vacuum is drawn on the bore to aspire the emulsified lens material and fluid coaxially through the ultrasonic tip.

Freeman in U.S. Pat. No. 4,808,154 describes a phacoemulsification/irrigation and aspiration sleeve apparatus having a hollow cylindrical base member operable to be connected to a hand piece of phacoemulsification/irrigation and aspiration unit. A tip or probe extends through the hollow cylindrical base and coaxially projects through a cylindrical sleeve member connected to the base. The cylindrical sleeve member has an internal diameter greater than the external diameter of the tip or probe thereby forming an annular passage around the tip member to conduct a lens flushing solution around the probe and into a zone of lens aspiration at the distal end of the tip member. The cylindrical sleeve is provided with at least one internal longitudinal extending rib member to guide the flushing fluid through the cylindrical member and to isolate interior wall portions of the cylindrical sleeve from the tip member.

Another phacoemulsifier ultrasonic handpiece is described by Banko in U.S. Pat. No. 3,805,787. Banko describes a handpiece having a number of attachments for use with an ultrasonic transducer, each attachment having an arrangement such that a shield of metallic material can be placed around a vibrating brobe and held in concentric relationship therewith. The attachments are such as to enable the delivery of irrigation fluid or suction pressure, either individually or in combination to desired points within the operating field.

One difference between the phacoemulsification devices and the current invention is that in phacoemulsification the area to be treated is very small. Phacoemulsification horns are from 0.063 to 0.125 inches in diameter and 0.5 to 1.5 inches in length; much smaller in both diameter and length than that required in ultrasonic liposuction devices. The ultrasonic disruption of large amounts of tissue requires horns of from 0.160 to 0.250 inches in diameter and from 6.0 to 15.0 inches in length. The larger diameter permits the transfer of more power to larger target areas. The longer length is required to allow the surgeon to treat a large area with only one incision. The presence of large amounts of power in the ultrasonic probe and working deep within tissue requires a method of isolating tissue from the probe for a distance of several wave lengths.

Another difference between the phacoemulsifcation devices described by Freeman and Banko and the current invention is that the ultrasonic horns used in lipectomy have no central bore for aspiration: dislodged fat passes into the space between the outer sleeve and the ultrasonic horn to a trap in the vacuum line. The annular sleeve around the ultrasonic tip conducts only body fluids and aspirated fatty tissue. While in phacoemulsification it is always important to cool the ultrasonic horn tip to prevent overheating of the eye, in lipectomy moderate heating at the tip where the cells are being removed is acceptable. The heating is caused by longitudinal vibrations of the horn. The current design also includes a longtudinal cannula for delivering fluid to flush and cool the target area is desired.

Another difference between the phacoemulsification device described by Freeman and the current invention is that the longitudinal rib member of the phacoemulsification device does not isolate the sleeve and surrounding tissue from energy transfer as do the nodal supporting mounts of the present invention. The sleeve mounting means described in the present invention provides a convenient means for mounting the sleeve while at the same time, enabling maximum power transfer to the longitudinal vibrational mode of the ultrasonic horn for the disruption and melting of fatty tissue. The sleeve of the phacoemulsification device become hot. This is acceptable in a device which does not pass through tissue but is not desirable in suction lipectomy, wherein the liposuction device must go through tissue exposing tissue to the effects of vibration (heat) along its length.

Phacoemulsifiers rely on the application of an ultrasonic field to disrupt and fragment a crystalline structure and the injection of fluid to emulsify the fragments for transport away from the operating site. thus, the tissue aspirate through the aspiration channel of a phacoemulsifier handpiece is a relatively homogeneous fluid and unlikely to clog the channel thereby rendering the cleaning of the channel simple. The tissue aspirate passing through the aspiration channel of a suction lipectomy handpiece, on the other hand, is a non-homogeneous suspension of disrupted tissue and blood. Such an aspirate can and does adhere to the inner walls of the aspirator channel making it difficult to clean.

MLC Technologies sales brochure for "ULTRAVAC Series Three General Suction System" describes an "UL TRAVAC" device which consists of an electronic console, and ultrasonic hand piece and a vacuum pump. The ultrasonic device uses the high frequency vibration to disrupt and separate the fatty tissues and creates localized heat through friction. The separated liquefied fatty tissue is then aspirated by the suction pump in a more liquid form than the old fashioned suction types. There have been problems wit breakage of the probes, which are not exponential in design, damage to tissue along the length of the probes because they are not isolated from the surrounding tissue, and corresponding lack of energy concentration at the tips of these devices.

Perdreaux, Jr. in U.S. Pat. No. 3,956,826, incorporated herein by reference, describes an ultrasonic dental cleaning device wherein the handpiece comprises an ultrasonic horn surrounded by an irrigation sleeve. The irrigation sleeve surrounds the ultrasonic probe defining a channel therebetween through which irrigating fluid may be conducted to the vicinity of the probe tip. Perdreaux, Jr. incorporates adjustables screws in the sleeve which make contact with the ultrasonic probe at a longitudinal vibrational node.

SUMMARY OF THE INVENTION

The present invention provides for an aspiration sleeve having a hollow cylindrical member which may be easily releasably connected to the hand piece of an ultrasonic liposuction device and aspiration unit. An ultrasonic transducer or probe extends through the hollow cylindrical sleeve and coaxially projects through the tip of the cylindrical sleeve member. The cylindrical sleeve member has an internal diameter greater than the greatest external diameter of the ultrasonic horn, thereby forming an annular passage or conduit around the ultrasonic horn to conduct disrupted tissue aspirated by vacuum through the tip to a trap in the vacuum line. In addition to having means for establishing a removable attachment to the handpiece, the cylindrical sleeve is provided with an internal mounting point or mounting points positioned so as to rest against the ultrasonic horn at a vibratory node or at vibratory nodes and thereby maximizing the transfer of energy to the tip of the horn and minimizing undersirable energy transfer to the sleeve with resultant trauma to tissue other than at the tip of the horn. The effective localization of energy at the tip of the horn made possible by this sleeve will permit more delicate, selective aspiration of adipose tissue and be less tiring to the surgeon.

Other objects, features and advantages of the invention will be readily apparent from the following description of certain preferred embodiments thereof taken in conjunction with the accompanying drawing although variations and modifications may be effected without departing from the spirit and scope of the concepts of the disclosure and in which:

DESCRIPTION OF PREFERRED EMBODIMENT

In view of the foreqoing problems associated with the current art and the improvement inherent in ultrasonic-assisted devices, it is one object of this invention to provide a sleeve for use with an ultrasonic horn used in a lipectomy cannula that will produce less pain and trauma to the patient. It is yet another object of this invention to provide a sleeve for use with an ultrasonic lipectomy device which will make the device less tiring to the surgeon to use. And, finally, it is also an object of this invention to provide a sleeve for use with an ultrasonic horn in a lipectomy cannula which will enable the surgeon to have increased precision and control of the probe and can be moved more slowly through the tissue while the ultrasound breaks up the fatty tissue.

Figure 1:
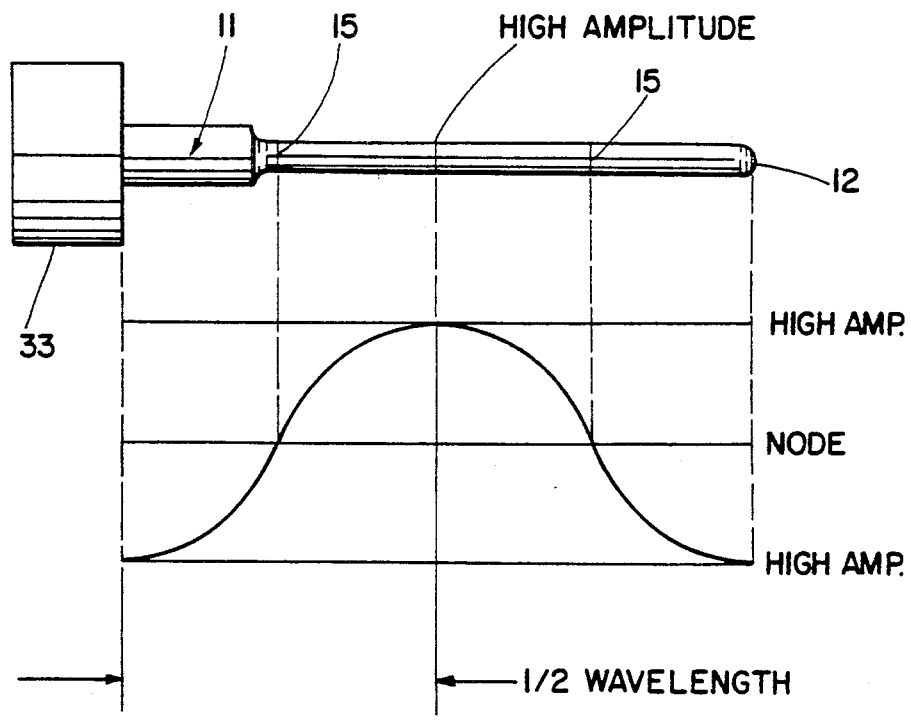
FIG. 1 is a vibrating ultrasonic horn showing the nodal planes spaced at one-half wavelength.

Turning now to FIG. 1, when an exponential horn (FIG. 1 (11)) is vibrated at its reasonant frequency, the end (12) lengthens and shortens. No longitudinal motion occurs at the horn's nodal plane or planes (15) which planes are spaced along the horn at intervals of one half the resonant wave length, but stress concentration is greatest here. Horn amplitude is measured as peak to peak displacement of the horn face. Amplitude is increased or decreased by changing the cross sectional area and mass distribution of the horn or by altering the input amplitude, the ratio of a horn's output amplitude to its input amplitude is called "gain."

Figure 2:
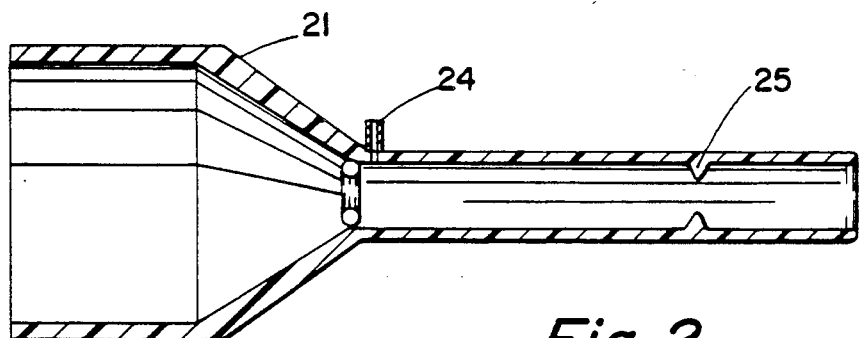
FIG. 2 is a cutaway side elevational view of an improved sleeve in accordance with the first preferred embodiment of this invention.

Turning now to FIG. 2, the sleeve of the instant invention (21) is seen in side elevation. A suction conduit (24) projecting from the sleeve is fitted with a vacuum connection. The sleeve support member(s) (25) extend radially inward from the interior surface of the sleeve member to touch the ultrasonic horn at a vibratory nodal plane(s).

Figure 3:
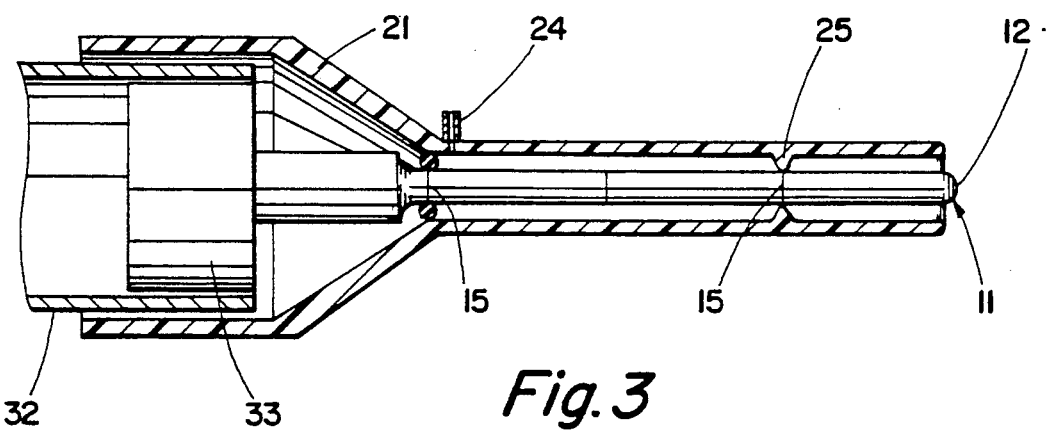
FIG. 3 is an cutaway side elevation of an ultrasonic liposuction hand piece and sleeve operable to remove fatty tissue from a patient.

Turning now to FIG. 3, the relationship between the ultrasonic horn (11), handpiece (32) and converter (33) of a conventional handpiece are shown. The nodal sleeve stabilizing mounts (25) inside the aspirator sleeve are positioned to rest upon the nodal plane (15) of the horn when the sleeve is properly positioned.

One advantage of the present invention is that the energy being generated at the handpiece is transferred without the interference and dissipation which would be caused by contact with the sleeve at other than the nodal planes.

Another advantage of the present invention is that the nodal stabilizing mounts in the sleeve isolate the energy of the horn from the tissue along its length, minimizing heating and cell disruption and damage other than at the target area.

Still another advantage of the present invention is that the ultrasonic horn may be manipulated more delicately than the unassisted suction lipectomy probe, facilitating more precise tissue aspiration.

Another advantage of the present invention is that it does not require the repeated forceful thrusting of conventional suction lipectomy, thus requiring less effort from the surgeon.

Yet another advantage of the present invention is that it creates a cannula which is prevented from occluding by the nodal sleeve stabilizing mounts.

Another advantage of the present invention, an acoustically isolated aspiration sleeve, is that other components such as an other sleeve containing an irrigation channel can be mounted on the aspiration sleeve with little chance of loss of energy to such components.

Still another advantage of the present invention is that it provides the ability to simultaneously flush and aspirate the area being treated if desired through separate channels/cannulas which can be mounted on the exterior surface of the aspiration sleeve.

Another advantage of the present invention is that the aspiration sleeve can be constructed of inexpensive materials such as plastic.

Yet another advantage of the present invention is that the aspiration sleeve can be manufactured as a disposable product, which eliminates the need for difficult and time-consuming cleaning and sterilization procedures.

Another advantage of the present invention in a disposable form is that it eliminates the possibility of cross-contamination of patients that could result from ineffective cleaning or sterilization of a nondisposable sleeve.

Still another advantage of the present invention is that the ultrasonic frequency and energy delivered at the tip of the ultasonic horn has been shown to very effectively disrupt adipose tissue cells while being less effective on connective (blood vessel, muscle) tissue. This reduces the danger of damage to connective tissue and excessive blood loss during the procedure.

Another advantage of the present invention is that until the present invention of an acoustically isolated sleeve, the benefits of ultrasonics in use for large area tissue disruption were not obtainable due to the problems associated with power loss and tissue damage along the ultrasonic horn.

In view of the considerations disclosed herein it is obvious that modifications may be made to the invention, such as having the support member extend radially outward from one or more vibrational nodes of the horn itself to contact the interior surface of the sleeve. Or separate inserts could be slipped over the horn and positioned over the vibratory nodes before the aspirator sleeve is positioned over the horn. Such modifications are suggested by the specification and claims and are included within the scope of the invention.

What we claim is:

1. In an ultasonic lipectomy device, which device includes a handpiece said handpiece comprising an ultrasonic electrostrictive converter element and a substantially cylindrical ultrasonic horn member connected to the converter element which has vibratory nodal planes at the points where no longitudinal motion is occurring, spaced along the horn at intervals of one half the resonant wave length, said horn member being structurally adapted to be inserted into fatty tissue underlying the skin for disrupting fatty tissue, the improvement comprising a removable displable aspiration sleeve said aspiration sleeve further comprising;
   (a) a hollow cylindrical base member operable to be releasably connected to the handpiece;
   (b) a hollow cylindrical sleeve member extending distally from said base member, said sleeve member being structurally adapted for insertion beneath the skin to coaxially and protectively surround the cylindrical ultrasonic horn, said sleeve member having an internal diameter greater than the external diameter of the cylindrical ultasonic horn member the difference in diameters providing an annular passage around the ultrasonic horn, said annular passage being operable to conduct a fatty tissue aspirate from the distal end of the ultrasonic horn to the base end; and
   (c) a sleeve support member or members extending radially inward from the interior surface of said sleeve member, said support member or members disposed within the sleeve to touch said untrasonic horn at one or more vibratory nodal planes of said horn.

2. The ultrasonic lipectomy device as set forth in claim 1, said aspiration sleeve member being composed of a material having a plastic composition.

* * * * *